United States Patent [19]

Eisenmann

[11] Patent Number: 4,789,338
[45] Date of Patent: Dec. 6, 1988

[54] DENTAL PROSTHESIS

[75] Inventor: Friedrich Eisenmann, Geislingen Steige, Fed. Rep. of Germany

[73] Assignee: Implantec GmbH, Fed. Rep. of Germany

[21] Appl. No.: 7,348

[22] Filed: Jan. 27, 1987

[51] Int. Cl.$^4$ ............................................. A61C 13/225
[52] U.S. Cl. .................................... 433/181; 433/169; 433/177
[58] Field of Search ............... 433/181, 182, 183, 180, 433/177, 178, 191, 192, 169

[56] References Cited

U.S. PATENT DOCUMENTS

| 1,664,726 | 4/1928 | Adler | 433/177 |
| 1,693,845 | 12/1928 | Kellner et al. | 433/182 |
| 1,753,644 | 4/1930 | Burden | 433/181 |
| 2,350,196 | 5/1944 | Saffir | 433/191 |
| 2,491,581 | 12/1949 | Reichner | 433/191 |
| 3,710,446 | 1/1973 | Poveromo | 433/182 |
| 4,362,509 | 12/1982 | Sulc | 433/169 |

Primary Examiner—John J. Wilson
Attorney, Agent, or Firm—Welsh & Katz, Ltd.

[57] ABSTRACT

A dental prosthesis having multiple components is provided with flexibility by connecting individual components of the prosthesis with flexible buffer components that are connected to the individual components of the prosthesis through dovetail slots that are located between adjacent components. The flexible buffer components are inserted in the dovetail slots to connect adjacent components of the prosthesis. The connection of tooth crowns and bridge components by the flexible means of the present invention fixes in place the remaining teeth to which the crown or bridge is connected but it preserves the flexibility of the teeth that support the crown or bridge. This contributes to a healthy mouth. The mobility of the dental prosthesis can be adjusted to approximate that of the normal teeth by varying the flexibility of the buffer part or parts.

11 Claims, 2 Drawing Sheets

DENTAL PROSTHESIS

This invention relates to connectors for dental prostheses. In particular, it relates to connectors for dental prosthesis in which multiple crowns or bridges are joined together.

Restorative dentistry has been characterized for many years by the use of permanently installed dental prostheses such as crowns and bridges. The use of solid cast crowns and metal-ceramic crowns has generally been in a one-piece casting in which the bridge system components are rigidly joined together. When the individual bridge components are connected, as by soldering, a single rigid unit is the result. In contrast, natural teeth are not anchored rigidly to the bone but are connected flexibly in a rather complicated manner through the periodontium. In addition, the alveolar bones anchoring the teeth are flexible, particularly those of the lower jaw. The alveolar bones can also respond to forces exerted on the bone from the teeth by resolution of part of the axial forces into longitudinal components. Thus, the generally axial force applied to each individual tooth is resolved through the flexibility and individual relative motion of each tooth with respect to the others.

The natural distribution of forces on teeth is affected by the use of rigidly connected multiple prostheses. This rigidity leads to the development of complaints by the wearers of such prostheses and to failures of the prostheses. Because of these problems, multiple bridges are often not recommended or used by practitioners.

SUMMARY OF THE INVENTION

It is an object of the present invention to provide a dental prosthesis having components that are not rigidly joined.

It is a further object of the present invention to provide a dental prosthesis that is coupled to the natural support system for the teeth so as to provide a flexible prosthesis.

A dental prosthesis having multiple components is provided with flexibility by joining individual components of the prosthesis with flexible buffers connected to the individual components of the prosthesis through dovetail slots located between adjacent components. The flexible buffers are inserted in the dovetail slots to connect adjacent components of the prosthesis. The connection of tooth crowns and bridges components by the flexible means of the present invention fixes in place the remaining teeth to which the crown or bridge is connected while preserving the flexibility of the teeth that support the crown or bridge. Such a structure contributes to a healthy mouth. The mobility of the dental prosthesis can be adjusted to approximate that of the normal teeth by varying the flexibility of the buffer part or parts.

The resulting flexibility of the dental prosthesis of the present invention reduces the problems of existing rigid bridges which can lead under some circumstances to bone damage or even to the shrinkage of bone. As a result, the dental prosthesis of the present invention can be expected to last longer than existing crowns and bridges. Another advantage of the dental prosthesis of the present invention comes from the fact that for the first time it has become possible to change, replace and renew crown or bridge parts after a crown or bridge has been installed in the mouth. In addition, it is possible to combine or connect a permanently installed crown or bridge with a removable prosthesis, providing an increased flexibility in dental care that could not be achieved before.

The advantages of the invention are achieved by the use of individual crown or bridge elements, one for each tooth to be replaced. The crown or bridge part is provided with a recess in the form of a dovetail slot. A flexible connecting buffer is adapted for insertion into the slots of adjacent parts. The slots may be placed between adjacent crown or bridge elements, and they may open toward the biting surfaces or toward the inside of the mouth. The latter approach is especially appropriate for the front teeth and for a bridge in which one or more teeth are not connected directly to natural teeth. In this case, a connecting member is slid into place from behind the teeth. For either direction of the slot, a step at the end of the slot supports the buffer in place.

In an alternate embodiment of the invention, secure seating of adjacent crowns or bridges using a buffer between them is provided by a slight taper of the slot. Buffers for placement between adjacent crowns or bridge parts may also be constricted in the middle part to form a natural continuaton of the gap between the teeth, thereby facilitating cleaning of the teeth. Buffers for connecting crowns or bridges may comprise a metal sleeve conforming to the slots. The buffer may have a secondary sleeve fitted over the buffer to provide a mating surface with the slot. In contrast, if the slot can readily be made to desired dimensions, then the metal sleeve and the secondary sleeve may be omitted and the buffer may be installed directly into the slot. It may be desirable to use cross pieces, pins, ribs, or the like to make a stronger joint between the buffer and the secondary sleeve. The buffer may be made of plastic, glass fiber material, a flexible metal, or any other elastic and yielding material that can safely be used in the mouth.

Flexibility of the buffers may be increased by the use of additional components such as spiral threads or elastic fiber bundles. The buffers may be formed of elastic bands, plastic, or metal strips, as desired and appropriate. it is possible to achieve flexibility with high strength by alternating plastic and metal strips.

DETAILED DESCRIPTION OF THE INVENTION

Figure 1:
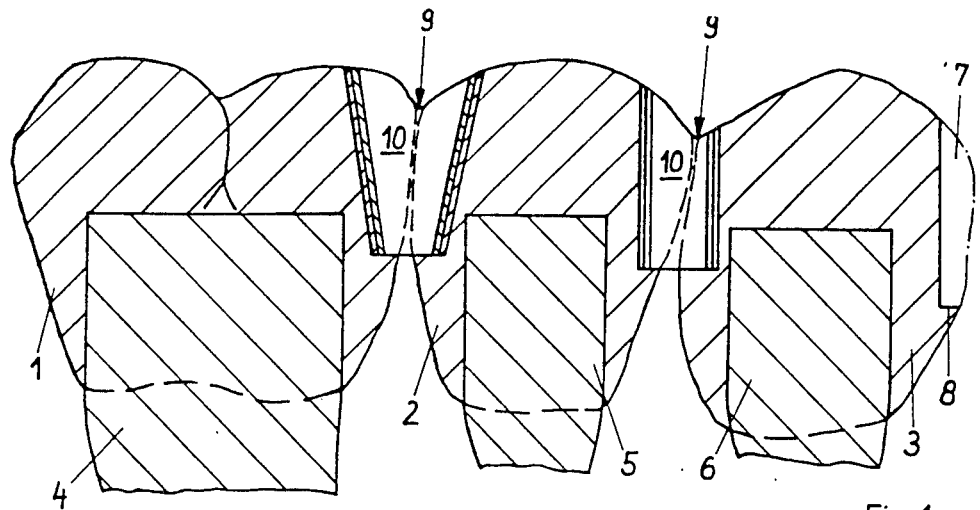
FIG. 1 is a longitudinal section through the dental prosthesis of the present invention.

FIG. 1 is a longitudinal section through the dental prosthesis of the present invention. In FIG. 1, crown 1 is seated on residual tooth 4, crown 2 is seated on residual tooth 5, and crown 3 is seated on residual tooth 6. Each of the crowns has a slot 7 on a side adjacent another one of the crowns. Each slot is open in the direction of the biting surface and is terminated at its other end by a step 8. Slot 7 may extend over the width of the entire tooth or it may extend over only a part of the width of the tooth. The slot 7 may be made with walls that are parallel or with a slight taper that narrows away from the biting surface. The invention is practiced by sliding a buffer 9 into the slot 7 in each of two adjacent crowns to join the crowns flexibly.

Figure 2:
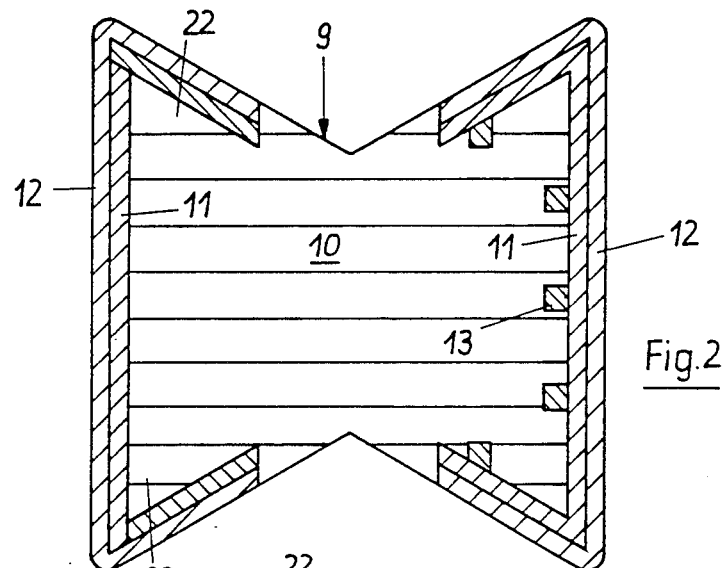
FIG. 2 is a sectional view through a buffer for the practice of the present invention.

FIG. 2 is a sectional view of a buffer for the practice of the present invention. In FIG. 2 an elastic core 10 is surrounded in part by a lining which consists of an inner secondary sleeve 11 that is covered by an outer metal sleeve 12. The secondary sleeve 11 may be made of any material, and is affixed to core 10, either directly or with the use of ribs 13. A secure joint between core 10 and secondary sleeve 11 prevents growth of bacteria in the joint.

Metal sleeve 12 is sized to provide a snug fit with slot 7. This provides a dimensionally stable surface against which to fit secondary sleeve 11 of buffer 9. Relative movement in the installation of buffer 9 takes place between the secondary sleeve 11 and the metal sleeve 12.

It can be seen from FIG. 2 that buffer 9 has a dovetail shape, with a constriction midway between its ends. Secondary sleeve 11 and metal sleeve 12 do not extend to the constriction, which allows the flexible material of core 10 to permit bending between adjacent crowns that are joined by the core 10.

Slot 7 in connecting crowns or bridges can be made in various ways, such as a wax molding, requiring that metal sleeve 12 be cemented or soldered into the crown. In the alternative, a crown may be cast onto a metal sleeve 12, or produced by spark erosion or the use of laser beams. If a sufficiently accurate and smooth slot 7 can be formed in a crown, then metal sleeve 12 may be eliminated and a buffer 9 may be installed directly in the slot. Similarly, if the material of buffer 9 is hard enough, then secondary sleeve 11 may be eliminated and the buffer 9 may be inserted directly in metal sleeve 12 or in slot 7. It is also possible to achieve a proper fit by casting a core material directly into a secondary sleeve 11 either before or after the crowns or bridge parts are fitted in place in the mouth.

Figure 3:
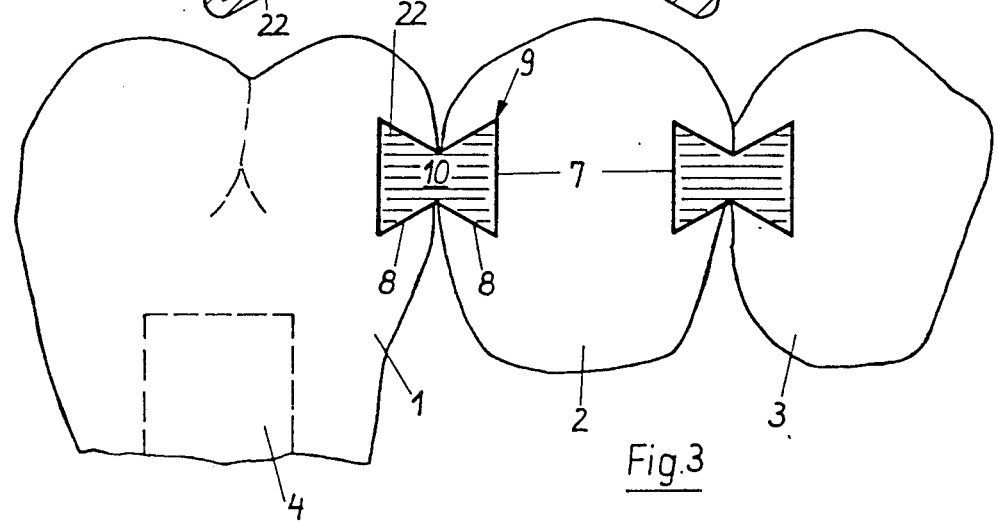
FIG. 3 is a rear view of an alternate embodiment of the prosthesis of the present invention.

FIG. 3 is a rear view of an alternate embodiment of the present invention. In FIG. 3, crown 1 is attached to residual tooth 4, while crowns 2 and 3 are not connected to residual teeth, but instead form a bridge. Slots 7 are placed parallel to the biting surfaces of the prosthesis and the buffer 9 is inserted laterally, substantially parallel to the surface of the gum, from inside the mouth. The embodiment of FIG. 3 is particularly appropriate for use in front teeth and for use with a prosthesis in which one or more of the residual teeth is missing, so that one or more false teeth may be installed between crowned teeth. In this case the false teeth are supported securely by lateral insertion of the buffer and by its dovetail shape. The elastic material of buffer 9 permits relative motion between adjacent crowns or prostheses.

Figure 4:
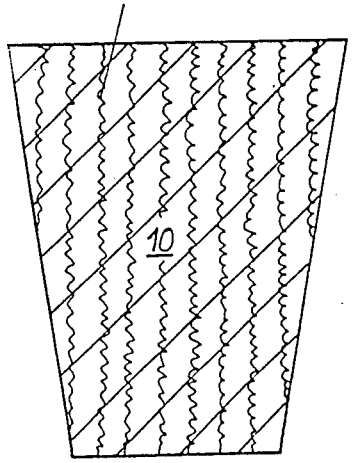
FIG. 4 is a sectional view of a flexible buffer showing the presence of spiral threads.

FIG. 4–7 represent alternate embodiments of buffer 9 and core 10. Core 10 of FIG. 4 is tapered and threads 13 run through core 10. Threads 13 may be arranged in spiral form or placed loosely in the interior of core 10. Threads 13 may be loose or bundled, and may or may not be prestressed. Threads 13 are disposed so as to be perpendicular to the biting surface of a crown when buffer 9 is used in the configuration of FIG. 1.

Figure 5:
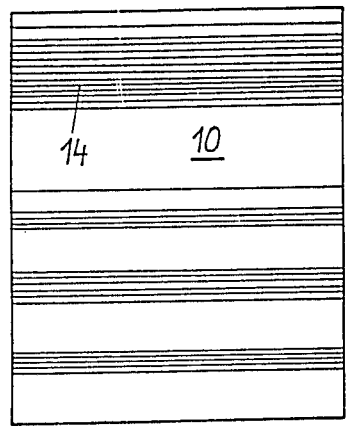
FIG. 5 is a side view of an alternate embodiment of a buffer for the practice of the present invention.

FIG. 5 is a side view of a core 10 in which threads 14, either individually or in bundles, are disposed so as to be parallel to the biting surface of a crown when used in the configuration of FIG. 1. This arrangement provides for elasticity of core 10.

Figure 6:
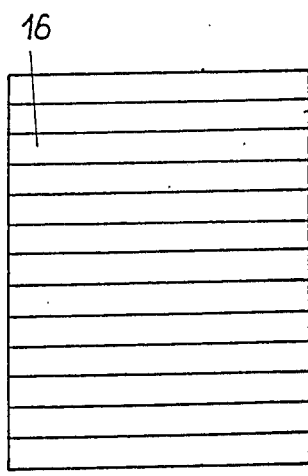
FIG. 6 is a side view of a second alternate embodiment of the buffer of the present invention.

FIG. 6 is an alternate embodiment of core 10 in which core 10 is formed of alternating metal bands 15 and plates 16, of either plastic or glass fiber. Plates 16 are connected to elastic metal bands 15 by gluing, cementing, or the like.

Figure 7:
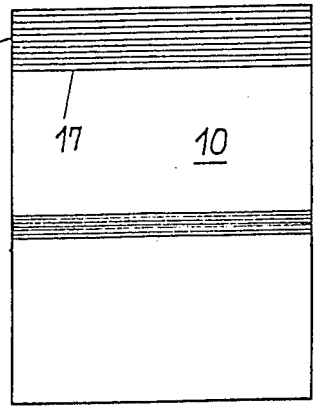
FIG. 7 is a side view of a third alternate embodiment of the buffer of the present invention.

FIG. 7 is an alternate embodiment of core 10 in which laminations 17 are cemented together to form the core 10. Laminations 17 may be cemented together only at their outer circumference, as by adhesive layer 18, or they may be joined by cement placed over the entire surface of each lamination 17.

Figure 8:
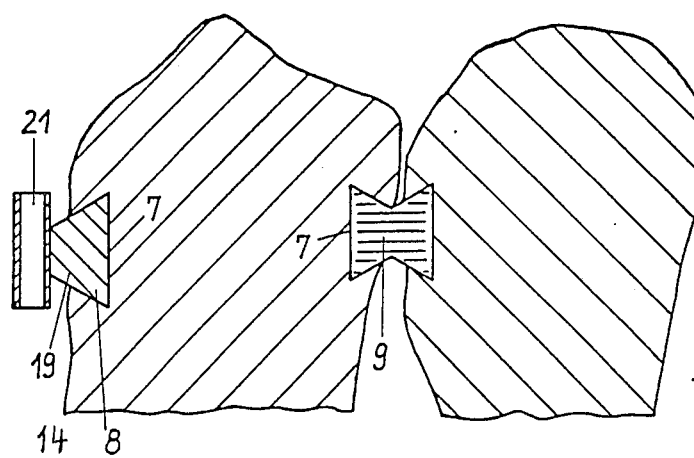
FIG. 8 is a sectional side view of the dental prosthesis of the present invention with a support.

Buffers 9 of the present invention are separable from other parts of the dental prosthesis. As a result, buffers 9 can be manufactured for use with any crown or bridge that is given a properly sized slot 7 to enable the interconnection of crowns. Similarly, individual components of dental prostheses can be changed readily. An example of the flexibility that is thereby made possible is shown in FIG. 8 which is a longitudinal section through the dental prosthesis of the present invention with a support. In FIG. 8 buffer 9 is shown in place joining two units of a prosthesis. A slot 7' may previously have contained a buffer 9 that has been removed to permit the insertion of a solid insert 19. Bore 21 of solid insert 19 is adapted to receive wires, pins, or the like to attach to the dental prosthesis.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A connector for flexible removable interconnection of dental units such as crowns and bridges, each dental unit including a biting surface and an axis that is substantially perpendicular to the biting surface, the connector comprising:
   (a) a slot in each of the dental units parallel to the axis, said slot open at a first end that is closer to said biting surface and closed with a step at an end opposite to said first end, said slots opposite each other in adjacent dental units, each of said slots undercut to form a dovetail cross-section;
   (b) a sleeve sized to fit in each of said slots; and
   (c) a flexible buffer means having dovetail cross-sections on opposite sides removably and slidably inserted into said sleeves in said slots in adjacent dental units to hold the dental units in side-by-side engagement.

2. The apparatus of claim 1 wherein said buffer means comprises an additional secondary sleeve sized for insertion into said slot.

3. The apparatus of claim 1 comprising in addition a metal sleeve sized for insertion into said slot and a secondary sleeve connected to said buffer means and sized to fit into said metal sleeve.

4. The apparatus of claim 3 wherein said secondary sleeve is affixed to said buffer means by ribs.

5. The connector for a dental prosthesis of claim 1 wherein said slots are tapered and wherein said buffer means is tapered to fit the tapered slots.

6. The connector for a dental prosthesis of claim 1 wherein said buffer means is constricted in a middle region.

7. The apparatus of claim 1 comprising in addition fiber bundles disposed in the buffer.

8. The connector for a dental prosthesis of a claim 1 comprising in addition spiral threads disposed in the buffer.

9. The connector for a dental prosthesis of claim 1 wherein said buffer means is formed of plastic strips.

10. The connector for a dental prosthesis of claim 1 wherein said buffer means is formed of metal strips.

11. The connector for a dental prosthesis of claim 1 wherein said buffer means is formed of alternating plastic and metal strips.

* * * * *